United States Patent [19]

Homma et al.

[11] Patent Number: 5,488,857
[45] Date of Patent: Feb. 6, 1996

[54] PROTRUSION SENSOR FOR SENSING PROTRUSION ON A DISC

[75] Inventors: Shinji Homma, Kanagawa; Kyoichi Mori, Hiratsuka; Takashi Nakakita, Hadano, all of Japan

[73] Assignee: Hitachi Electronic Engineering Co., Ltd., Tokyo, Japan

[21] Appl. No.: 350,034

[22] Filed: Nov. 29, 1994

Related U.S. Application Data

[63] Continuation of Ser. No. 977,634, Nov. 17, 1992, abandoned.

[30] Foreign Application Priority Data

Nov. 22, 1991 [JP] Japan ................................ 3-334319
Nov. 22, 1991 [JP] Japan ................................ 3-334320

[51] Int. Cl.⁶ ................................................ G01B 17/08
[52] U.S. Cl. ................................................ 73/105; 73/660
[58] Field of Search ................................ 73/104, 105, 660

[56] References Cited

U.S. PATENT DOCUMENTS

| | | | |
|---|---|---|---|
| 2,405,133 | 8/1946 | Brown | 73/105 |
| 2,460,726 | 2/1949 | Arndt, Jr. | 73/105 |
| 2,728,222 | 12/1955 | Becker et al. | 73/105 |
| 3,049,002 | 8/1962 | Hediger | 73/105 |
| 3,112,642 | 12/1963 | Harmon et al. | 73/105 |
| 3,504,552 | 4/1970 | Hiller | 73/105 X |
| 3,793,627 | 2/1974 | Darrel et al. | 73/104 X |
| 3,872,285 | 3/1975 | Shum et al. | 73/104 X |
| 4,532,802 | 8/1985 | Yeack-Scranton et al. | 73/866.4 |
| 5,168,412 | 12/1992 | Doan et al. | 73/105 X |
| 5,237,861 | 8/1993 | Suda et al. | 73/105 |

FOREIGN PATENT DOCUMENTS

| | | | |
|---|---|---|---|
| 372690 | 6/1990 | European Pat. Off. | 73/105 |
| 238447 | 8/1986 | Germany | 73/660 |
| 135402 | 8/1983 | Japan | 73/105 |
| 61-151456 | 7/1986 | Japan . | |
| 61-227220 | 10/1986 | Japan . | |
| 131898 | 4/1961 | U.S.S.R. | 73/105 |
| 1504485 | 8/1989 | U.S.S.R. | 73/105 |
| 594308 | 11/1947 | United Kingdom | 73/105 |

*Primary Examiner*—Thomas P. Noland
*Attorney, Agent, or Firm*—Fay, Sharpe, Beall, Fagan, Minnich & McKee

[57] ABSTRACT

A protrusion sensor according to the present invention comprises a protrusion sensing head, a suspension spring having a front end portion fixedly mounting the protrusion sensing head and a rear end portion fixedly secured to one surface of a support arm, a carriage for supporting the support arm and a vibration sensor of piezo-electric ceramics fixedly mounted on the other surface of the support arm. A protrusion is detected by the collision of the protrusion sensing head flying by air flow on a surface of a rotary disc caused by rotation thereof with a protrusion.

11 Claims, 5 Drawing Sheets

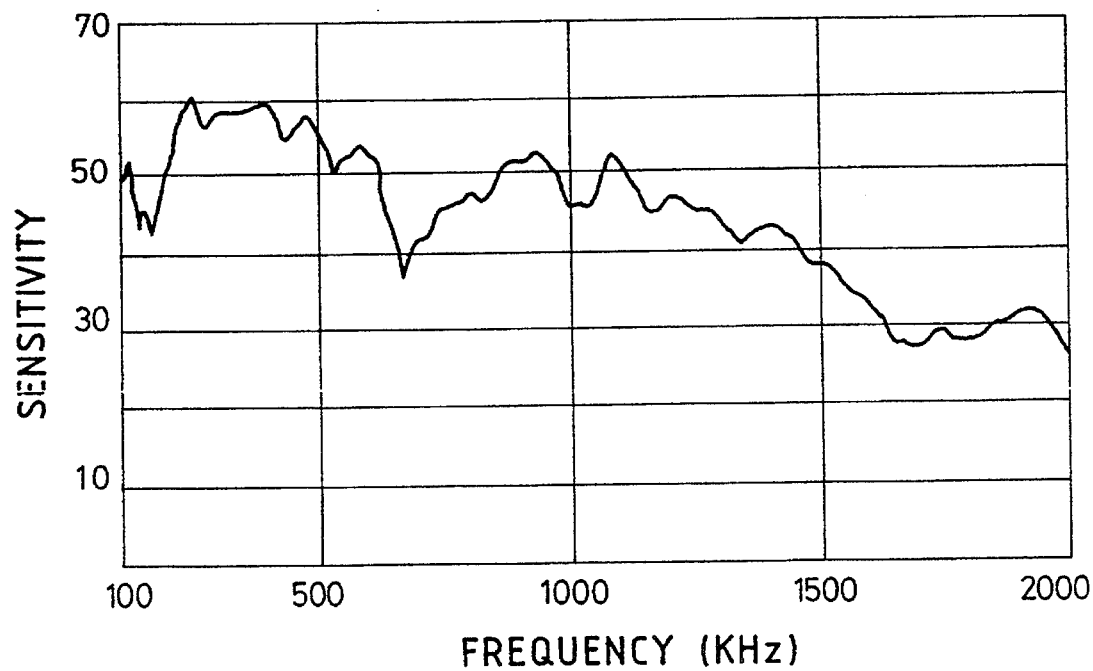

PROTRUSION SENSOR FOR SENSING PROTRUSION ON A DISC

This is a continuation application of Ser. No. 07/977,634, filed Nov. 17, 1992 and now abandoned.

BACKGROUND OF THE INVENTION

Technical Field

The present invention relates to a protrusion sensor for sensing a protrusion on a disc and, particularly, to a protrusion sensor for sensing fine protrusions or projections (hereinafter, simply called "protrusions" in this specification and claims) on a magnetic disc with high precision, without the necessity of mounting a vibration sensor on a protrusion sensing head.

Background Art

A magnetic disc which is of the information recording media type is constructed with a disc base of aluminum or glass, a magnetic film formed on one surface thereof and a protective film formed on the magnetic film. It is desired that the surface has no unevenness and is as flat as possible. In order to obtain such a flat surface, the magnetic disc is cleaned. However, it has been known that, even after the cleaning, there may be protrusions of a certain size left thereon. When a magnetic disc having such residual protrusion is used, a magnetic head may be damaged by collision with the protrusions. Furthermore, there may be a problem of error generation in accessed data.

In order to avoid such problems, magnetic discs manufactured are usually tested for protrusions. When a predetermined number of protrusions having size larger than a certain size are left on the magnetic disc, it is cleaned again.

FIGS. 4(a) to 4(c) show the protrusion sensing mechanism portion of a conventional glide tester and the sensing operation thereof. In FIG. 4(a), a magnetic disc 1 having a magnetic film and a protective film thereon is mounted on a spindle 2 and rotated thereby. A carriage mechanism 7 is provided in an opposing relation to the side portion of the magnetic disc 1, and one end of a support arm 6 is fixedly secured to a moving portion 7a of the carriage mechanism 7. The rear end of a suspension spring 5 is fixedly secured to the lower surface of the other end portion of the support arm 6. A protrusion sensing head 3 is mounted on the front end of the suspension spring 5 such that it rests on the disc surface.

When the magnetic disc 1 is rotated by the spindle 2, the protrusion sensing head 3 flies or is lifted up from the surface of the magnetic disc by air flow caused by the rotation of the magnetic disc. The suspension spring 5 biases the sensing head 3 downwardly such that the flying height of the sensing head 3 measured from the disc surface becomes a predetermined value. The glide tester converts the vibration of the sensing head 3 caused by a collision with any protrusion on the rotating disc into an electrical signal which is used to detect the protrusion.

In relation to the magnetic head for accessing the magnetic disc and the reading/writing of data, there is the formerly used Winchester type and recently developed thin film type. FIG. 4(b) shows a protrusion sensing head 3 suitable for use with the Winchester type magnetic head and FIG. 4(c) shows that suitable for the thin film magnetic head. As shown in FIGS. 4(a) to 4(c), these protrusion sensing heads 3 have sliders 3a which are identical in configuration to the magnetic heads, respectively. A piezo-electric transducer 4 is fixedly secured on the slider 3a of the protrusion sensing head 3. The piezo-electric transducer 4 may be of piezo-electric ceramics such as quartz having a monocrystalline structure.

The protrusion sensing head 3 is moved radially of the magnetic disc 1 by the moving portion 7a driven by a driving motor 7b, as shown by an arrow R in FIG. 4(a), so that the protrusion sensing head 3 scans the surface of the magnetic disc 1 spirally or coaxially. The protrusion sensing head 3 flies at a height δh by air flow caused by rotation of the magnetic disc 1 as shown in FIGS. 4(b) and 4(c). When there is any protrusion whose height is not less than δh on the disc surface, the slider 3a collides with it and a vibration is generated thereby in the piezo-electric transducer 4. A voltage signal is derived from the piezo-electric transducer with which a protrusion detection circuit determines presence of a protrusion.

FIG. 5(a) shows an example of the protrusion detection circuit of the glide tester. The circuit includes an amplifier 8a connected to the piezo-electric transducer 4, a detection circuit 8b including a band-pass filter BPF and an envelope detection circuit DET, and a comparator 8c having a threshold voltage Sv set to obtain a protrusion detection signal.

The slider 3a vibrates when the protrusion sensing head 3 collides with a protrusion on the surface of the magnetic disc 1, and the vibration is transmitted to the piezo-electric transducer 4 on the slider 3a. Therefore, the piezo-electric transducer 4 converts the vibration into a voltage signal Vfc having a specific frequency fc which may be in the order of 100 KHz to 300 KHz, as shown in FIG. 5(b). The output voltage of the piezo-electric transducer 4 is amplified by the amplifier 8a and a relatively low frequency component of the amplified voltage is derived by the band-pass filter BPF of the detection circuit 8b and its envelope is detected by the envelope detector DET, resulting in a voltage signal Vfl of low frequency fl, as shown in FIG. 5(c).

The output voltage Vfl is supplied to the comparator 8c and compared with the threshold voltage Sv thereof. When the voltage Vfl is larger than the threshold voltage Sv, as shown by a dotted line, the comparator 8c provides a protrusion detection pulse P which is supplied to a data processing portion 20 in which the protrusion detection pulses P are counted, the count being used to determine the quality of the magnetic disc.

In the protrusion detection mechanism mentioned above, the piezo-electric transducer 4 is mounted on the protrusion sensing head 3 and exerts an additinal load thereon. Since an actual magnetic head has no such piezo-electric transducer, there may be a case where the flying attitude of the protrusion sensing head with respect to the rotating magnetic disc is different from that of the actual magnetic head and the detected height of protrusion differs from actual height. Further, the piezo-electric transducer 4 may be damaged by collision with a protrusion, causing data obtained to be unreliable. In addition to this, since the piezo-electric transducer 4 is connected to the amplifier 8a of the protrusion detection circuit 8 through very thin lead wires, they may be easily broken by shock of collision. In either case, a damaged piezo-electric transducer and/or broken lead wires must be replaced by new ones, which is troublesome.

Recently, magnetic heads have become more and more compact due to the increase of information recording density on a magnetic disc. For example, very small magnetic heads having thicknesses of 0.5 mm and areas of 2 mm×2.6 mm have been realized. With such small magnetic heads, the flying height δh of the magnetic head with respect to the magnetic disc becomes as small as 0.05 μm. In such a case, the size of protrusion sensing heads also becomes very small correspondingly. Therefore, an upper limit of tolerable protrusion size becomes 0.05 μm. The protrusion detection mechanism is required to respond to such small protrusion.

Such very small protrusion sensing heads as mentioned above have substantially no space for mounting a piezo-electric transducer unless the latter is very small. However, the smaller the piezo-electric transducer, the lower the sensitivity. In such case, the above mentioned problem of difference in flying attitude between the protrusion sensing head and an actual magnetic head may become larger when a smaller sensing head having a piezo-electric transducer of usual size is used, causing the reliability of test data to be degraded.

Summary of the Invention

An object of the present invention is to provide a protrusion sensor which is capable of sensing fine protrusions on a disc with high sensitivity and in which there is no need of mounting a vibration sensor on the protrusion sensing head thereof.

Another object of the present invention is to provide a protrusion detection mechanism which is capable of sensing fine protrusion on a disc with high sensitivity and in which there is no need of mounting a vibration sensor on a protrusion sensing head thereof.

A further object of the present invention is to provide a protrusion detection circuit capable of detecting fine protrusion on a magnetic disc with high sensitivity.

A still further object of the present invention is to provide a glide tester for sensing protrusions on a magnetic disc which is capable of sensing fine protrusions with high sensitivity and in which there is no need of mounting a vibration sensor on the protrusion sensing head thereof.

The protrusion detection mechanism according to the present invention is featured by comprising a protrusion sensing head, a suspension spring having a front end fixedly mounted to the protrusion sensing head and a rear end fixedly secured to the lower surface of the front end of a support arm and a vibration sensor of piezo-electric ceramics fixedly secured to the upper surface of the front end of the support arm.

The protrusion sensing head of FIG. 1a does not bear the vibration sensor. Furthermore, the thickness of the portion of the support arm on which the piezo-electric ceramics is fixed is substantially equal to a half wavelength or an integer multiple of a half wavelength of a longitudinal ultrasonic wave having a frequency within the receivable frequency band of the vibration sensor. These ultrasonic waves are generated by collisions with protrusions and propagate through the support arm.

The protrusion detection circuit of the present invention improves the detecting performance for fine protrusions by deriving a specific frequency component of the output voltage of the vibration sensor by removing the noise component contained therein, differentiating the specific frequency component and comparing it with a predetermined level. That is, the protrusion detection circuit includes an amplifier for amplifying an electric signal obtained from the vibration sensor, a band-pass filter for deriving the component having frequency specific to the vibration sensor from the amplified signal, a detection circuit for detecting an envelope of an output signal of the band-pass filter and outputting a voltage signal representative thereof, a differentiator circuit for differentiating the voltage signal and a comparator for comparing an output signal of the differentiator circuit with a predetermined threshold value and outputting a pulse indicative of presence of a protrusion when the output signal of the differentiator is larger than the predetermined threshold value.

The protrusion sensor according to the present invention comprises the protrusion detection mechanism alone or the protrusion detection mechanism and the protrusion detection circuit.

In the present invention, the vibration sensor of piezo-electric ceramics is mounted on the support arm. The thickness of the support arm is set to a value substantially equal to a half wavelength or an integer multiple of half wavelength of a longitudinal ultrasonic wave having a frequency within the receivable frequency range of the vibration sensor so that an ultrasonic wave in the longitudinal direction generated by a collision with a protrusion becomes a standing wave.

With this construction, it is possible to transmit an ultrasonic wave generated when the protrusion sensing head collides with a protrusion to the support arm through the suspension spring such that the support arm stores only such a longitudinal acoustic wave having a wavelength equal to an integer multiple of half wavelength corresponding to the thickness of the support arm by resonance. The vibration sensor formed of a piezo-electric ceramics having specific frequency or high harmonics thereof corresponding to a resonance frequency of the support arm responds to collision energy efficiently and detects collisions reliably.

Therefore, there is no need of directly mounting a vibration sensor on the protrusion sensing head and thus the size of the slider, etc., can be minimized. Due to the fact that the vibration sensor is not mounted on the slider, the latter can fly with respect to a rotating disc with its attitude substantially the same as that of an actual magnetic head, so that the detection of protrusions on a magnetic disc becomes possible with high accuracy.

BRIEF DESCRIPTION OF THE DRAWINGS

FIG. 3 is a graph showing a frequency vs. sensitivity characteristics of the ultrasonic sensor of the protrusion detection mechanism shown in FIG. 1(a);

DETAILED DESCRIPTION OF THE PREFERRED EMBODIMENTS

Figure 1A:
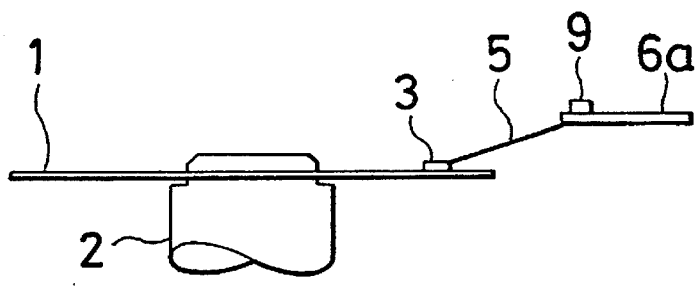
FIG. 1(a) shows a protrusion detection mechanism of a glide tester according to an embodiment of the present invention.
Figure 4A:
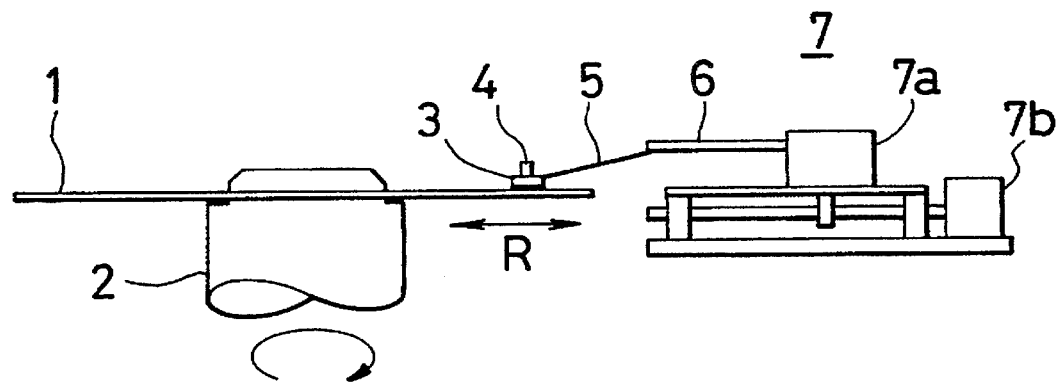
FIG. 4(a) shows a protrusion detection mechanism of a conventional glide tester.

In FIG. 1(a) which corresponds to FIG. 4(a) showing the conventional arrangement, a protrusion sensing head 3 has no piezo-electric transducer mounted thereon contrary to the conventional arrangement. An ultrasonic sensor 9 is mounted on the front end portion of the support arm 6a. Other constructive members and arrangements thereof are the same as those shown in FIG. 4(a) and therefore details thereof are omitted here.

In the present invention, the thickness of the support arm 6a is important.

Figure 4B:
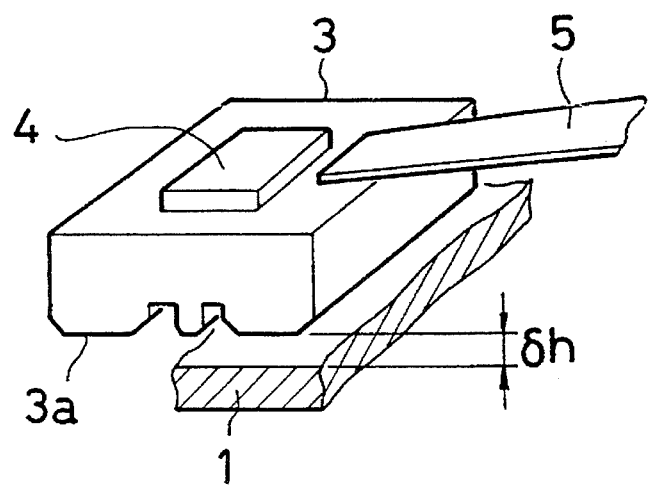
FIG. 4(b) shows a conventional head slider of the Winchester type.
Figure 4C:
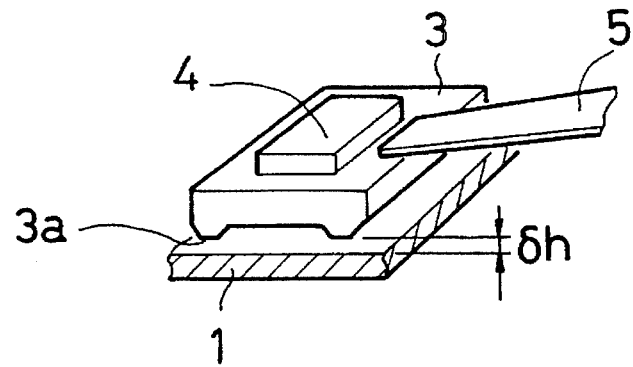
FIG. 4(c) shows a conventional thin film head.

The protrusion sensing head 3 which may have a configuration and size suitable for use with either the Winchester type shown in FIG. 4(b), the thin film type shown in FIG. 4(c), or a very small head as mentioned previously is mounted on the front end portion of the suspension spring 5. A rear end portion of the suspension spring 5 is fixedly secured to the lower surface of the front end portion of the support arm 6a having its rear end portion fixed to a carriage 7 (not shown in FIG. 1(a)). The support arm 6a is made from an aluminum plate on which an ultrasonic sensor 9 of piezo-electric ceramics such as polycrystalline ceramics of barium titanate or lead zirconate titanate is fixedly secured as a vibration sensor. The ultrasonic sensor 9 is a longitudinal wave probe having a specific vibration frequency (or resonance frequency) $fcn$ expressed by the following equation (1):

$$fcn = (n/2d) \cdot (E^{1/2}/\rho) \qquad \ldots (1)$$

where d is thickness of the sensor 9, n is a positive integer, E is Young's modulus of the sensor material and $\rho$ is the density thereof.

Figure 1B:
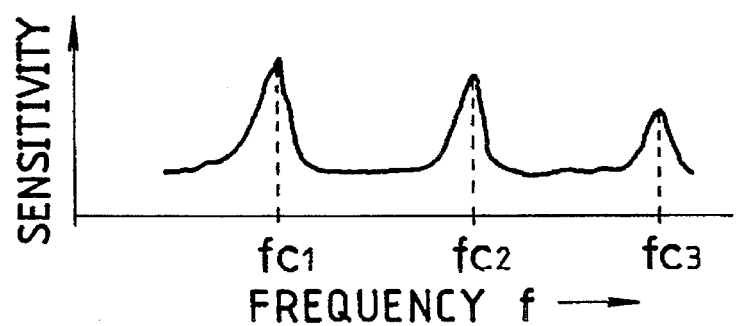
FIG. 1(b) is a graph showing a specific vibration frequency of an ultrasonic sensor of the protrusion detection mechanism in FIG. 1(a)
Figure 1C:
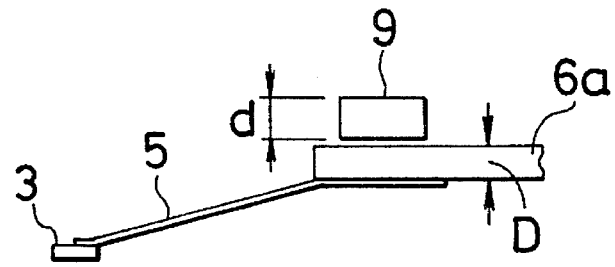
FIG. 1(c) shows the protrusion detection mechanism in FIG. 1(a) in more detail.

It should be noted that a gap between the ultrasonic sensor 9 and the support arm 6a shown in FIG. 1(c) is exaggerated for clarifying the relation between the thickness d of the sensor and the thickness D of the support arm. Since the gap corresponds to the thickness of an adhesive such as cyanoacrylate adhesive for fixing the sensor to the support arm, it is practically negligible.

FIG. 1(b) shows the frequency vs. sensitivity characteristics of the ultrasonic sensor 9. In general, the sensitivity of an ultrasonic sensor at frequency $fcn$ is at least several times that of a piezo-electric monocrystalline ceramics such as quartz. In this embodiment, the ultrasonic sensor 9 may have specific frequencies in a range from 100 KHz to 500 KHz which is substantially equal to or slightly higher than that of the conventional piezo-electric transducer used for the same purpose.

Among the specific frequencies $fcn$, a fundamental frequency $fc1$ (n=1) is obtained empirically or from a catalog, and the thickness D of the portion of the support arm 6a on which the ultrasonic sensor 9 is to be mounted is determined according to the following equations (2) and (3):

$$D = 2 \, m \times \lambda 1/4 \qquad \ldots (2)$$

$$\lambda 1 = v/fc1 \qquad \ldots (3)$$

where m is a positive integer, v is the propagation speed of the ultrasonic wave through the support arm, $\lambda 1$ is a wavelength corresponding to the frequency $fc1$ in the support arm.

Figure 1D:
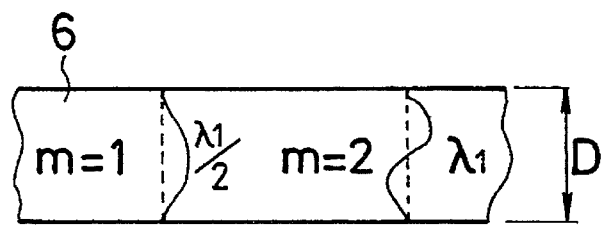
FIG. 1(d) illustrates longitudinal ultrasonic wave standing in a support arm of the protrusion detection mechanism in FIG. 1(a) in thickness direction thereof.

FIG. 1(d) illustrates the thickness vibration of the support arm 6a having thickness $D=\lambda 1/2$ and $D=\lambda 1$ for m=1 and m=2, respectively. That is, each of the support arms 6a having thickness $D=\lambda 1/2$ and $D=\lambda 1$ resonates at frequency $fc1 = v/\lambda 1$ and transmits a signal component vibrating at the fundamental frequency $fc1$ among vibration frequencies generated by the protrusion sensing head with minimum attenuation. Therefore, a longitudinal ultrasonic standing wave having the frequency $fc1$ exists in the support arm 6a and the ultrasonic sensor 9 converts the vibration frequency into a vibration voltage corresponding thereto.

When the support arm 6a is of aluminum and it is assumed that Young's modulus E of the support arm at room temperature is 7000 kgf/mm², Poisson ratio $\gamma$ thereof is 0.4 and density $\rho$ thereof is 2.7 g/cm³, propagation velocity v of an ultrasonic longitudinal wave through the support arm 6a can be expressed by the following equation:

$$\begin{aligned}
v &= [(1-\gamma)/(1+\gamma)(1-2\gamma)]^{1/2} \times (E/\rho)^{1/2} \\
&= [(1-0.4)/\{(1+0.4)(1-2\times 0.4)\}]^{1/2} \times \\
&\quad (6.86 \times 10^{10} \, [\text{N m}^{-2}]/2.7 \times 10^3 \, [\text{Kg m}^{-3}])^{1/2} \\
&= 7378 \, [\text{m/sec}]
\end{aligned}$$

Assuming $fc1=490$ KHz, the thickness D of the support arm 6a, that is, a half wavelength corresponding thereto becomes as follows:

$$\begin{aligned}
\lambda 1/2 &= v/2fc1 = 7378 \, [\text{m/sec}]/2 \times 49 \times 10^3 \, [\text{sec}^{-1}] \\
&= 7.53 \times 10^{-3} \, [\text{m}] \\
&= 7.53 \, [\text{mm}]
\end{aligned}$$

Therefore, the ultrasonic sensor 9 of this embodiment has a center frequency in a frequency range including the resonance frequency of 490 KHz and the thickness D of the portion of the support arm 6a on which the ultrasonic sensor 9 is to be mounted is set to at least substantially 7.53 mm. Since the temperature at which the protrusion sensor is usually used is regulated to (23°±3°) C., temperature variation in such range does not provide a considerable variation of longitudinal acoustic wave velocity for protrusion detection.

In this embodiment, since the thickness D of the support arm 6a and the resonance frequency of the ultrasonic sensor 9 provide the function of a filter, it is possible to obtain a detection signal having high SN ratio.

When it is difficult to obtain the thickness D of the support arm by calculation using the above equations, it is possible to determine the optimum thickness D with which highest sensitivity is obtained, by measuring sensitivity at frequency $fc1$ while changing the thickness.

FIG. 3 shows the frequency vs. sensitivity characteristics of the ultrasonic sensor 9. As shown in FIG. 3, it is preferable that the sensor is responsive to a frequency within a range from about 100 KHz to about 1.5 MHz. Therefore, the thickness of the support arm 6a may be from 2.5 mm (=7.5 mm/3.0, for 1.5 MHz) to 37 mm (=7.5 mm×4.9, for 100 KHz) although this thickness range may depend upon material of the support arm.

Figure 5A:
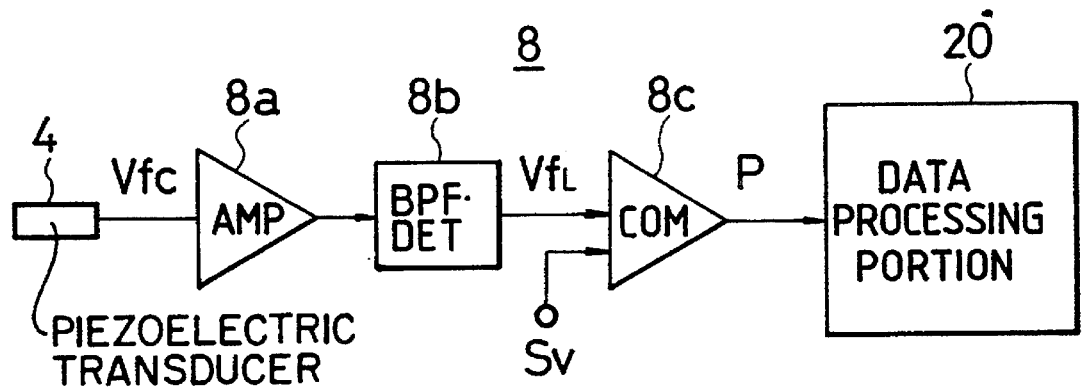
FIG. 5(a) is a block circuit diagram of a conventional protrusion detection circuit.
Figure 5B:
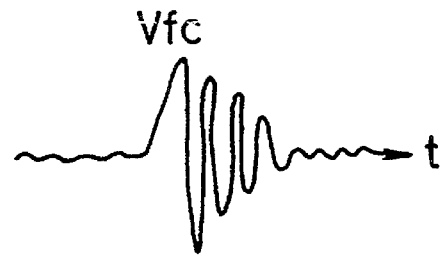
FIG. 5(b) shows vibration waveform of a conventional protrusion sensing head.
Figure 5C:
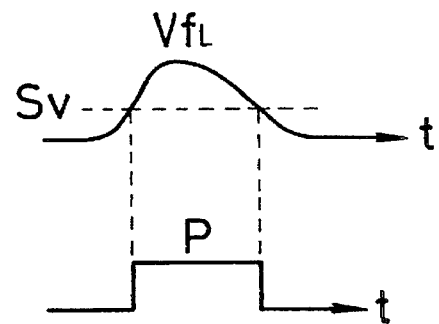
FIG. 5(c) illustrates an operation of the conventional protrusion sensing head.

The protrusion detection circuit shown in FIG. 5(a) may be used for processing an output of the ultrasonic sensor 9.

Figure 2A:
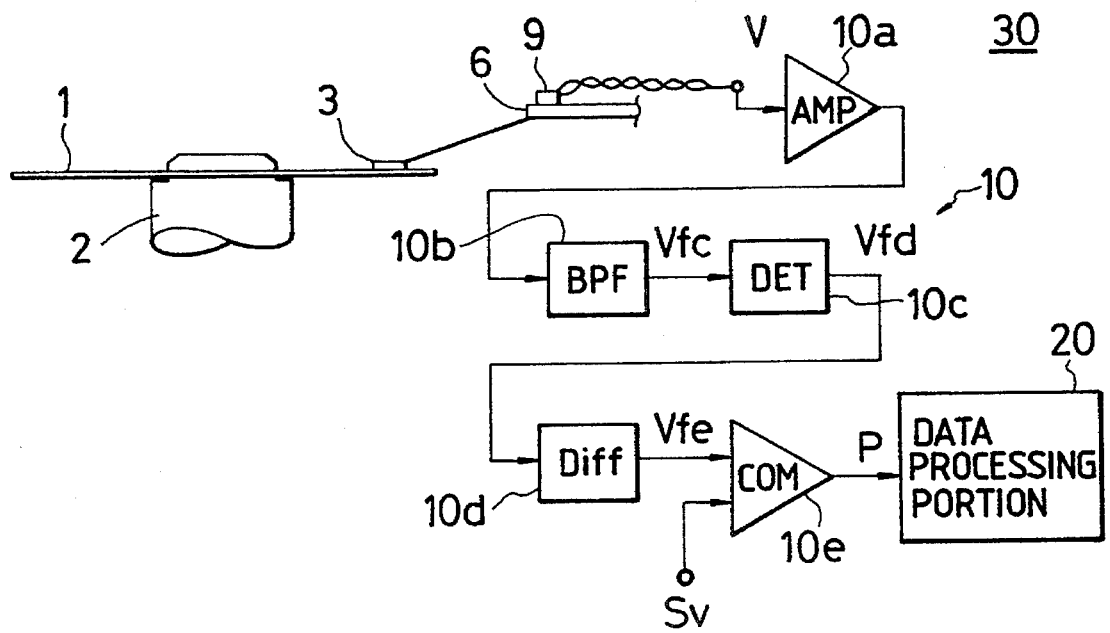
FIG. 2(a) is a block circuit diagram of an embodiment of a protrusion detection circuit of the glide tester.

However, it is preferable to use a protrusion detection circuit shown in FIG. 2(a). In FIG. 2(a), the glide tester 30 includes the protrusion detection circuit 10 and a data processing portion 20. The data processing portion 20 includes a microprocessor, a memory and a display device such as a printer or a CRT device. The protrusion detection circuit 10 is composed of an amplifier 10a, a band-pass filter (BPF) 10b, an envelope detection circuit (DET) 10c, a differentiator (Diff) 10d and a comparator (COM) 10e, all of which are connected in series in the described order. The comparator 10e has a constant threshold voltage Sv. In FIG. 2(a), the mechanical portions of the protrusion sensor are not shown for simplicity of illustration.

Figure 2B:
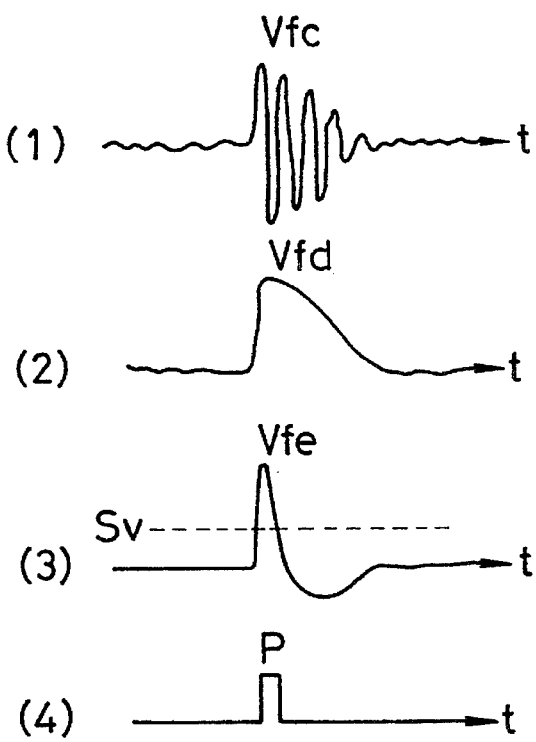
FIG. 2(b) shows signal waveforms in various operation steps of the protrusion detection circuit.

Describing an operation of the protrusion sensor in FIG. 2(a) by referring waveforms shown in FIG. 2(b), an output voltage signal V supplied from the ultrasonic sensor 9 and containing noise component is amplified to a suitable level by the amplifier 10a. An output of the amplifier 10a is passed through the band-pass filter 10b to remove the noise component. A resultant vibration voltage signal Vfc having its fundamental specific vibration frequency fc1 or a high harmonic fcn thereof is shown by a waveform (1) in FIG. 2(b).

The output signal of the band-pass filter 10b is supplied to the detection circuit 10c by which an envelope voltage signal Vfd thereof is obtained. The envelope signal Vfd is shown by the waveform (2) in FIG. 2(b). The envelope signal Vfd is supplied to the differentiator 10d in which it is differentiated to produce a differentiated voltage signal Vfe which emphasizes voltage change as shown by the waveform (3) in FIG. 2(b). The signal Vfe is compared by the comparator 10e with its threshold voltage Sv. The comparator 10e provides a protrusion detection pulse P when the signal Vfe is larger than the threshold voltage Sv, as shown by the waveform (4) in FIG. 2(b).

In the detection mechanism in which the ultrasonic sensor 9 is mounted on the support arm 6a, shock energy at a time when the protrusion sensing head 3 collides with protrusion is transmitted to the ultrasonic sensor 9 with minimum attenuation. As a result, such signal as the voltage signal Vfc shown in FIG. 2(b) which exhibits sharp rise is obtained and thus its envelope Vfd is also sharp as shown by the waveform (2). By differentiating it, the signal Vfe having high peak level is obtained and when the peak level is higher than the threshold voltage Sv of the comparator 10e, the latter provides the sharp signal P whose width is very narrow correspondingly to the sharpness of the voltage signal Vfe, improving the sensitivity and reliability. In this case, the frequency range of the filter 10b should be selected from a catalog thereof or empirically according to the specific vibration frequency fc1 or any high harmonic fcn thereof of the ultrasonic sensor 9 such that a low frequency component can be obtained. Further, the threshold voltage Sv of the comparator 10e can be determined suitably empirically.

With the embodiment, protrusion detection for a magnetic disc having a magnetic film and a protective coating has been described. However, it is obvious for those skilled in the art that the present invention can be applied to a protrusion detection for a substrate of such magnetic disc as well as discs other than magnetic discs.

In the protrusion detection mechanism described hereinbefore, the support arm 6a having a thickness resonating at the specific vibration frequency thereof is used to transmit vibration of the protrusion sensing head 3 to the ultrasonic sensor 9 with minimum attenuation and protrusions whose height is in the order of 0.05 μm is detected reliably by the protrusion detection circuit.

However, the transducer of piezo-electric ceramics is not always limited to the ultrasonic sensor. As a transducer for detecting ultrasonic wave, any piezo-electric ceramics can be used so long as its mechanical Q at a predetermined frequency is high and detection sensitivity is high. For ultrasonic sensor, titanate compounds such as barium titanate, lead zirconate titanate are preferable due to high sensitivity. For other applications, materials belonging to $Pb(Nb_{2/3}Ni_{1/3})O3$ group which is used for a ceramics filter can be used.

The piezo-electric ceramics is not always mounted on the upper surface of the front end portion of the support arm. It is possible to mount it on a lower surface of the front end portion with the rear end portion of the suspension spring being fixed to the upper surface of the support arm. Further, the support arm may be formed of materials other than aluminum.

Although, in this embodiment, the responsive frequency range of the ultrasonic sensor has been described as from 200 KHz to 700 KHz and the present invention has been described with using 490 KHz as example, a range from 100 KHz to 1.5 MHz can be used.

What is claimed is:

1. A protrusion sensor for detecting a protrusion on a surface of a rotary disc, comprising:

a protrusion sensing head;

a suspension spring having a front end portion fixedly mounted to said protrusion sensing head and a rear end portion fixedly secured to a surface of a support arm; and an ultrasonic sensor being fixedly mounted on an opposite surface of said support arm and having a receivable frequency range from 100 kHz to 1.5 MHz;

said protrusions being detected by the collisions of said protrusion sensing head flying by air flow on said surface of said rotary disc caused by rotation of said rotary disc with said protrusion.

2. The protrusion sensor claimed in claim 1, wherein a thickness of a portion of said support arm on which said ultrasonic sensor is fixedly mounted is substantially equal to a half wavelength of a longitudinal ultrasonic wave, or an integer multiple thereof.

3. The protrusion sensor claimed in claim 1, wherein said rotary disc is a magnetic disk, and said support arm is of aluminum having thickness from 2.5 mm to 37 mm.

4. The protrusion sensor claimed in claim 3, wherein said ultrasonic sensor is a transducer of a titanate compound.

5. The protrusion sensor claimed in claim 4, wherein the titanate compound is barium titanate.

6. The protrusion sensor claimed in claim 4, wherein the titanate compound is lead zirconate titanate.

7. A protrusion sensor for detecting a protrusion on a rotary disc substrate by the collisions of a protrusion sensing head flying by air flow caused by rotation of said rotary disc substrate with the protrusion, comprising:

said protrusion sensing head;

a suspension spring having a front end portion fixedly mounting said protrusion sensing head and a rear end portion fixedly secured to a surface of a support arm;

a carriage for supporting said support arm; and an ultrasonic sensor being fixedly mounted on an opposite surface of said support arm and having a receivable frequency range from 100 kHz to 1.5 MHz;

a thickness of a portion of said support arm on which said ultrasonic sensor is fixedly mounted being substantially equal to half wavelength of a longitudinal ultrasonic wave, or an integer multiple thereof.

8. The protrusion sensor claimed in claim 7, wherein said protrusion sensor is a glide tester.

9. A protrusion detection mechanism for detecting a protrusion on a rotary disc substrate by the collisions of a protrusion sensing head flying by air flow caused by rotation of said rotary disc substrate with the protrusion, comprising:

said protrusion sensing head;

a suspension spring having a front end portion fixedly mounting said protrusion sensing head and a rear end portion fixedly secured to a surface of a support arm;

a carriage for supporting said support arm; and an ultrasonic sensor being fixedly mounted on an opposite surface of said support arm and having a receivable frequency range from 100 kHz to 1.5 MHz;

a thickness of a portion of said support arm on which said ultrasonic sensor is fixedly mounted being substantially equal to a half wavelength of a longitudinal ultrasonic wave, or an integer multiple thereof.

10. A protrusion detection circuit for detecting a protrusion on a rotary disc substrate on the basis of an electric signal converted by a vibration sensor from vibrations generated by the collisions of a protrusion sensing head flying by air flow caused by rotation of said rotary disc substrate with the protrusion, comprising:

an amplifier for amplifying said electric signal;

a band-pass filter for filtering an output of said amplifier to derive vibration frequency component specific to said vibration sensor;

a detection circuit for detecting an envelope of an output signal of said band-pass filter and providing a voltage signal corresponding thereto;

a differentiator circuit for differentiating said voltage signal; and a comparator for comparing an output signal of said differentiator with a predetermined threshold value to provide a pulse indicative of a protrusion detection;

said vibration sensor being of piezo-electric ceramics and is fixedly mounted on a surface of a support arm for supporting said protrusion sensing head through a suspension spring having a rear end portion fixedly secured to an opposite surface of said support arm;

a thickness of a portion of said support arm on which said vibration sensor is fixedly mounted being substantially equal to a half wavelength of a longitudinal ultrasonic wave, or an integer multiple thereof.

11. The protrusion detection circuit claimed in claim 10, wherein said vibration sensor is an ultrasonic sensor.

\* \* \* \* \*